(12) United States Patent
Randle (10) Patent No.: US 11,267,141 B2
(45) Date of Patent: Mar. 8, 2022

(54) ARTICULATION FOR SURGICAL ROBOT

(71) Applicant: CMR Surgical Limited, Cambridge (GB)

(72) Inventor: Steven James Randle, Warwick (GB)

(73) Assignee: CMR Surgical Limited, Cambridge (GB)

( * ) Notice: Subject to any disclaimer, the term of this patent is extended or adjusted under 35 U.S.C. 154(b) by 1078 days.

(21) Appl. No.: 15/519,381

(22) PCT Filed: Sep. 29, 2015

(86) PCT No.: PCT/GB2015/052828
§ 371 (c)(1),
(2) Date: Apr. 14, 2017

(87) PCT Pub. No.: WO2016/059369
PCT Pub. Date: Apr. 21, 2016

(65) Prior Publication Data
US 2017/0245949 A1 Aug. 31, 2017

(30) Foreign Application Priority Data
Oct. 15, 2014 (GB) .................................... 1418257

(51) Int. Cl.
*B25J 17/02* (2006.01)

(52) U.S. Cl.
CPC ................... *B25J 17/0291* (2013.01)

(58) Field of Classification Search
CPC ............... A61B 34/30; A61B 2034/305; B25J 17/0291; B25J 17/0283; B25J 17/0275
See application file for complete search history.

(56) References Cited

U.S. PATENT DOCUMENTS 4,686,866 A * 8/1987 Rosheim ................. B25J 9/104
74/490.06
4,878,393 A * 11/1989 Duta .................... B25J 17/0275
74/490.06

(Continued)

FOREIGN PATENT DOCUMENTS

CN 103029119 A * 4/2013
CN 104889976 A * 9/2015 ........... F16M 11/123

(Continued)

OTHER PUBLICATIONS

GB Search Report for GB Patent Appl. No. 1418257.0, dated Mar. 8, 2016.

(Continued)

*Primary Examiner* — Jake Cook
*Assistant Examiner* — Gregory Robert Weber
(74) *Attorney, Agent, or Firm* — Rothwell, Figg, Ernst & Manbeck, P.C.

(57) ABSTRACT

A surgical robotic component comprising an articulated terminal portion, the terminal portion comprising: a distal segment having an attachment for a surgical tool; a basal segment for attaching the terminal portion to the remainder of the surgical robotic component; and an intermediate compound joint between the distal segment and the basal segment, the intermediate compound joint permitting relative rotation of the distal segment and the basal segment about first, second and third axes; the terminal portion being arranged such that, in at least one configuration of the intermediate compound joint: (i) the axial direction of the basal segment is parallel to the axial direction of the distal segment, and (ii) the first, second and third axes are transverse to the axial directions of the basal and distal segments.

16 Claims, 5 Drawing Sheets

(56) References Cited

U.S. PATENT DOCUMENTS

| | | | | |
|---|---|---|---|---|
| 4,911,033 | A * | 3/1990 | Rosheim | B25J 9/06 74/490.03 |
| 5,617,762 | A * | 4/1997 | Kirsch | B25J 17/0283 248/183.2 |
| 5,735,627 | A * | 4/1998 | Nagao | B25J 17/0283 285/147.3 |
| 5,898,599 | A * | 4/1999 | Massie | B25J 9/1689 318/628 |
| 5,966,991 | A * | 10/1999 | Gosselin | F16M 11/123 248/661 |
| 6,699,177 | B1 | 3/2004 | Wang et al. | |
| 6,699,235 | B2 * | 3/2004 | Wallace | A61B 34/70 606/1 |
| 6,793,669 | B2 * | 9/2004 | Nakamura | A61B 17/29 606/205 |
| 9,481,094 | B2 * | 11/2016 | Hirano | B25J 9/0051 |
| 2008/0245175 | A1 | 10/2008 | Jinno et al. | |
| 2011/0106302 | A1 * | 5/2011 | Long | B25J 17/0291 700/245 |
| 2011/0130212 | A1 * | 6/2011 | Sholev | B25J 17/0275 464/150 |
| 2012/0042628 | A1 * | 2/2012 | Rosheim | B25J 17/0266 60/232 |
| 2012/0316560 | A1 | 12/2012 | Hassoun | |
| 2013/0325032 | A1 * | 12/2013 | Schena | A61B 34/30 606/130 |
| 2014/0060234 | A1 * | 3/2014 | Uemura | B25J 11/00 74/490.05 |
| 2015/0082934 | A1 * | 3/2015 | Trui | B25J 9/0048 74/490.01 |
| 2016/0030268 | A1 * | 2/2016 | Meuleman | A61H 3/00 601/27 |

FOREIGN PATENT DOCUMENTS

| | | | | |
|---|---|---|---|---|
| DE | 102013021830 | A1 * | 6/2015 | B25J 17/0275 |
| GB | 2464147 | A * | 4/2010 | F16M 11/123 |
| GB | 2522951 | A | 8/2015 | |
| GB | 2523224 | A | 8/2015 | |
| WO | 2015/107326 | A1 | 7/2015 | |
| WO | 2015/132549 | A1 | 9/2015 | |
| WO | 2016/020456 | A1 | 2/2016 | |

OTHER PUBLICATIONS

EP International Search Report for PCT/GB2015/052828 dated Mar. 30, 2016.

EP Written Opinion for PCT/GB2015/052828 dated Mar. 30, 2016.

* cited by examiner

FIG. 6

ARTICULATION FOR SURGICAL ROBOT

This invention relates to surgical articulations, for example for use in surgical robotic components.

BACKGROUND

Figure 1:
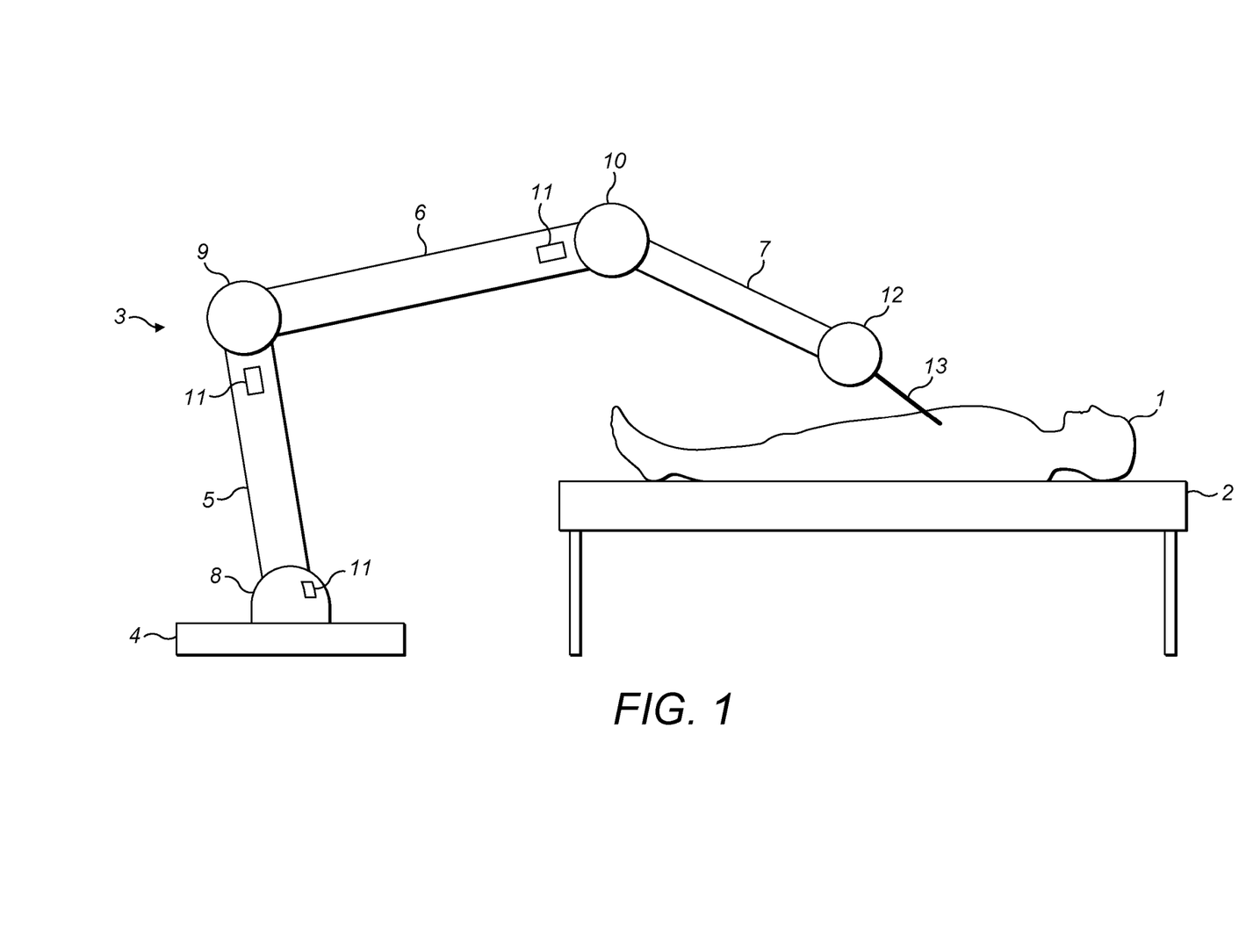
FIG. 1 shows a surgical robot arm.

FIG. 1 illustrates a typical surgical robot arm. A patient 1 is lying on a bed 2. The robot arm 3 extends from a base 4 towards the patient. The arm has a series of rigid links 5, 6, 7 which are connected to each other and to the base by articulations 8, 9, 10. The articulations provide a sufficient range of motion that the arm can approach the patient in different ways so as to perform a range of surgical procedures. The links can be made to move about the articulations by motors 11 which are under the control of a surgeon. The final link 7 of the arm terminates in a wrist articulation 12 to which a surgical instrument 13 is attached. The surgical instrument is designed for insertion into the patient and terminates in an end effector for performing or aiding the surgery, for example an endoscope or a cutting tool or pinching tool.

It is desirable for the wrist articulation 12 to be highly mobile, so that the end effector can be placed in a wide range of orientations relative to the final link of the arm. It is also desirable for the wrist joint 12 to be kinematically well-functioning, without there being any attitudes in the core of their range of motion that are difficult to reach or where there could be poor control over the motion of the end effector.

Figure 2:
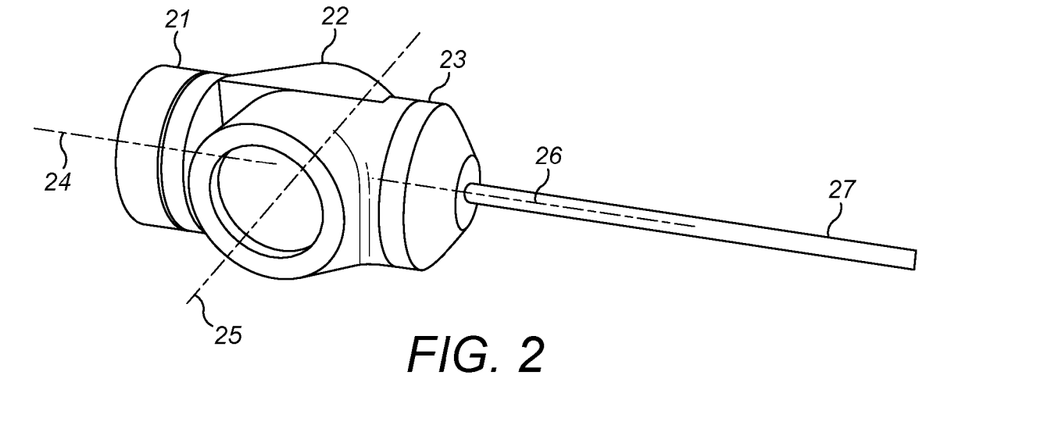
FIG. 2 shows a robotic component wrist.

FIG. 2 illustrates a typical wrist articulation. This wrist comprises two different types of joints: a "roll" joint which permits rotation about an axis generally along the arm, and a "pitch" joint which permits rotation about an axis generally transverse to the arm. The roll joints are indicated as 21 and 23 and the pitch joint is indicated as 22. With the wrist in the configuration shown in FIG. 2, the axes of the joints 21, 22 and 23 are indicated as 24, 25 and 26 respectively. This wrist gives an instrument 27 the freedom of movement to occupy a hemisphere whose base is centred on axis 24. However, this wrist is not well suited for use in a surgical robotic component. One reason for this is that when the pitch joint 22 is offset by just a small angle from the straight position shown in FIG. 2 a large rotation of joint 21 is needed to produce some relatively small lateral movements of the tip of the instrument. In this condition, when the pitch joint is almost straight, in order to move the end effector smoothly in a reasonable period of time the drive to joint 21 must be capable of very fast operation. This requirement is not readily compatible with making the links small and lightweight because it calls for a relatively large drive motor and sufficiently stiff links and articulations that the motor can react against them without jolting the position of the robotic component.

There is a need for a surgical robot arm and also surgical instruments that can successfully perform a wider range of surgical procedures than existing ones.

SUMMARY OF THE INVENTION

According to one aspect of the invention, there is provided a surgical robotic component comprising an articulated terminal portion, the terminal portion comprising: a distal segment having an attachment for a surgical tool; a basal segment for attaching the terminal portion to the remainder of the surgical robotic component; and an intermediate compound joint between the distal segment and the basal segment, the intermediate compound joint permitting relative rotation of the distal segment and the basal segment about first, second and third axes; the terminal portion being arranged such that, in at least one configuration of the intermediate compound joint: (i) the axial direction of the basal segment is parallel to the axial direction of the distal segment, and (ii) the first, second and third axes are transverse to the axial directions of the basal and distal segments.

Suitably, in the at least one configuration of the intermediate compound joint, the first, second and third axes are co-planar with each other. In the at least one configuration of the intermediate compound joint, the first, second and third axes may be perpendicular to the axial directions of the basal and distal segments.

Suitably, in the at least one configuration of the intermediate compound joint, the axial direction of the basal segment is collinear with the axial direction of the distal segment.

Suitably, the first, second and third axes intersect each other. The first, second and third axes may be co-planar with each other and offset from each other in that plane by 60°.

Suitably, the intermediate compound joint comprises: a first revolute joint which enables the distal segment to rotate about the first axis relative to the basal segment; a second revolute joint which enables the distal segment to rotate about the second axis relative to the basal segment; and a third revolute joint which enables the distal segment to rotate about the third axis relative to the basal segment.

The first, second and third revolute joints may be arranged to be independently driven.

Suitably, the surgical robotic component comprises a first drive shaft located in the basal segment for driving the first revolute joint, a second drive shaft located in the distal segment for driving the second revolute joint, and a third drive shaft located in the basal segment for driving the third revolute joint.

Suitably, the terminal portion comprises an additional revolute joint between the distal segment and the attachment, which permits rotation of the attachment about the axial direction of the distal segment.

Suitably, the only means of articulating the attachment relative to the basal segment are the intermediate compound joint and the additional revolute joint.

Suitably, the intermediate compound joint comprises a first intermediate segment and a second intermediate segment, the first intermediate segment coupled to the basal segment and separately coupled to the second intermediate segment, and the second intermediate segment coupled to the distal segment and separately coupled to the first intermediate segment. The first intermediate segment may comprise a basal arm portion coupled to the basal segment such that motion of the basal arm portion is restrained to rotation about the first axis relative to the basal segment. The second intermediate segment may comprise a distal arm portion coupled to the distal segment such that motion of the distal arm portion is restrained to rotation about the second axis relative to the distal segment.

Suitably, the first intermediate segment comprises a first connecting arm portion and the second intermediate segment comprises a second connecting arm portion, the first connecting arm portion coupled to the second connecting arm portion such that motion of the first connecting arm portion is restrained to rotation about the third axis relative to the second connecting arm portion.

The surgical robotic component may be a surgical robot arm. The surgical tool may be a surgical instrument which terminates in a surgical end effector.

The surgical robotic component may be a surgical instrument suitable for being driven by a surgical robot arm. The surgical tool may be a surgical end effector.

BRIEF DESCRIPTION OF THE DRAWINGS

The invention will now be described by way of example with reference to the accompanying drawings. In the drawings.

DETAILED DESCRIPTION

Figure 3:
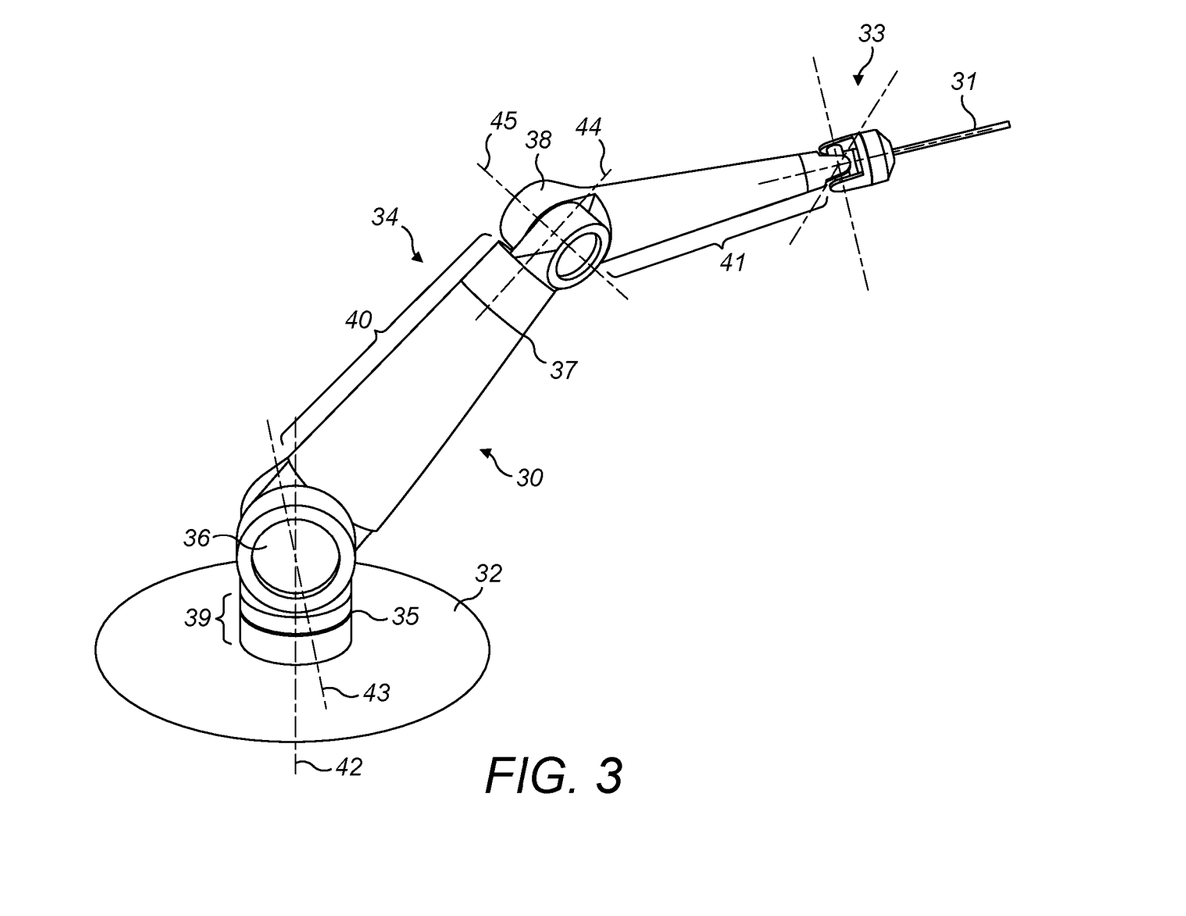
FIG. 3 shows a robot arm having a surgical instrument attached thereto.

FIG. 3 shows an exemplary robot arm (indicated generally at 30) having a surgical instrument 31 attached thereto. The robot arm extends from a base 32. The base could be mounted to the floor of an operating theatre, or to a fixed plinth, could be part of a mobile trolley or cart, could be mounted to a bed or could be mounted to the ceiling of an operating room. The base is fixed in place relative to the patient's bed or chair when an operation is being carried out. The robot arm comprises a wrist portion shown generally at 33 and a main portion shown generally at 34. The main portion makes up the majority of the extent of the arm and terminates at its distal end in its attachment to the wrist portion. The proximal end of the main portion is attached to the base. The wrist portion makes up the distal part of the arm and is attached to the distal end of the main portion.

The main portion of the arm comprises four joints 35, 36, 37, 38 and three shaft sections 39, 40, 41. The joints are revolute joints. The shaft sections are rigid, with the exception of joints 35 and 37 which are set into shaft sections 39 and 40 respectively. Each shaft section may have substantial length, and serve to provide the arm with reach and the ability to offset the wrist laterally and/or vertically from the base. The first shaft section could be truncated relative to the second and third shaft sections if the base is located in a suitable place; particularly if the base is elevated from the floor.

The first shaft section 39 is attached to the base 32. In practice the first shaft section can conveniently extend in a generally upright direction from the base but it could extend at a significant incline to vertical, or even horizontally.

Joint 35 is located in the first shaft section. Joint 35 permits relative rotation of the proximal part of the first shaft section, which is fixed to the base, and the remainder of the arm about an axis 42. Conveniently, axis 42 is parallel with or substantially parallel with the main extent of the first shaft section in forming the arm, which runs from the base towards joint 36. Thus, conveniently the angle of axis 42 to the main extent of the first shaft section in forming the arm could be less than 30°, less than 20° or less than 10°. Axis 42 could be vertical or substantially vertical. Axis 42 could extend between the base and joint 36.

Joint 36 is located at the distal end of the first shaft section 39. Joint 36 permits relative rotation of the first shaft section 39 and the second shaft section 40, which is attached to the distal end of joint 36, about an axis 43 which is transverse to the first shaft section 39 and/or the second shaft section 40. Conveniently axis 43 is perpendicular or substantially perpendicular to either or both of the first and second shaft sections. Thus, conveniently the angle of axis 43 to the main extents of either or both of the first and second shaft sections could be less than 30°, less than 20° or less than 10°. Conveniently axis 43 is perpendicular or substantially perpendicular to axis 42 and/or to the axis 44 to be described below.

Joint 37 is located in the second shaft section. Joint 37 permits relative rotation of the proximal part of the second shaft section and the remainder of the arm about an axis 44. Conveniently, axis 44 is parallel with or substantially parallel with the main extent of the second shaft section. Thus, conveniently the angle of axis 44 to the main extent of the second shaft section could be less than 30°, less than 20° or less than 10°. Axis 44 could intersect or substantially intersect (e.g. within 50 mm of) axis 43 and the axis 45 that will be described below. In FIG. 3 joint 37 is shown located closer to the distal end of the second shaft section than the proximal end. This is advantageous because it reduces the mass that needs to be rotated at joint 37, but joint 37 could be located at any point on the second shaft section. The second shaft section is conveniently longer than the first shaft section.

Joint 38 is located at the distal end of the second shaft section 40. Joint 38 permits relative rotation of the second shaft section and the third shaft section 41, which is attached to the distal end of joint 38, about an axis 45 which is transverse to the second shaft section 40 and/or the third shaft section 41. Conveniently axis 45 is perpendicular or substantially perpendicular to either or both of the second and third shaft sections. Thus, conveniently the angle of axis 45 to the main extents of either or both of the second and third shaft sections could be less than 30°, less than 20° or less than 10°. Conveniently axis 45 is perpendicular or substantially perpendicular to axis 44.

In summary, then, in one example the main portion of the arm can be composed as follows, in order from the base to the distal end of the main portion:

1. a first shaft section 39 having substantial or insubstantial length and containing a joint 35 that permits rotation e.g. about an axis generally along the extent (if any) of the first shaft section in forming the arm (a "roll joint");

2. a joint 36 permitting rotation transverse to the first shaft section and/or to the axis of the preceding joint (joint 35) and/or to the axis of the succeeding joint (joint 37) (a "pitch joint");

3. a second shaft section 40 having substantial length and containing a joint 37 that permits rotation about an axis generally along the extent of the second shaft section and/or to the axis of the preceding joint (joint 36) and/or to the succeeding joint (joint 38) (a roll joint);

4. a joint 38 permitting rotation transverse to the second shaft section and or to the preceding joint (joint 37) and/or to the succeeding joint (joint 38) (a pitch joint); and 5. a third shaft section 41 having substantial length.

The wrist portion 33 is attached to the distal end of the third shaft section. An example of the wrist portion is shown in more detail in FIG. 5.

Figure 4:
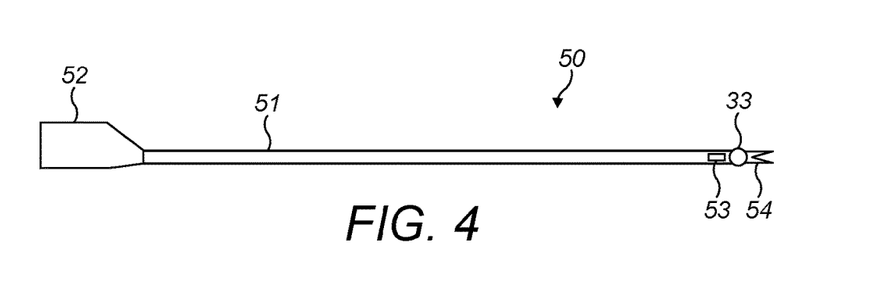
FIG. 4 shows a surgical instrument.

FIG. 4 illustrates an exemplary surgical instrument, shown generally at 50. The surgical instrument 50 comprises an instrument base 52, an elongate instrument shaft 51, a wrist portion 33, and an end effector 54. The end effector 54 can be made to move about the wrist articulation 33 by motor 53 which is under the control of a surgeon via the robot arm. The end effector could, for example, be a gripper, a pair of shears, a camera, a laser or a knife. An example of the wrist portion 33 is shown in more detail in FIG. 5.

Figure 5A:
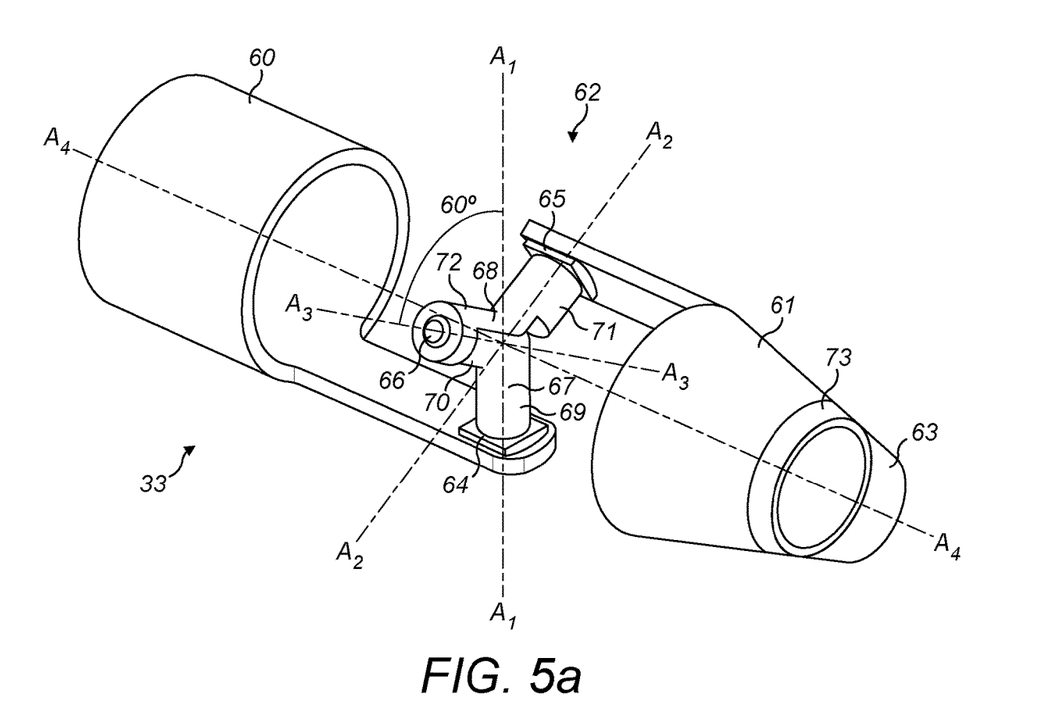
FIG. 5 shows a robotic wrist component. The wrist is illustrated in three different configurations at FIGS. 5a, 5b and 5c.
Figure 5B:
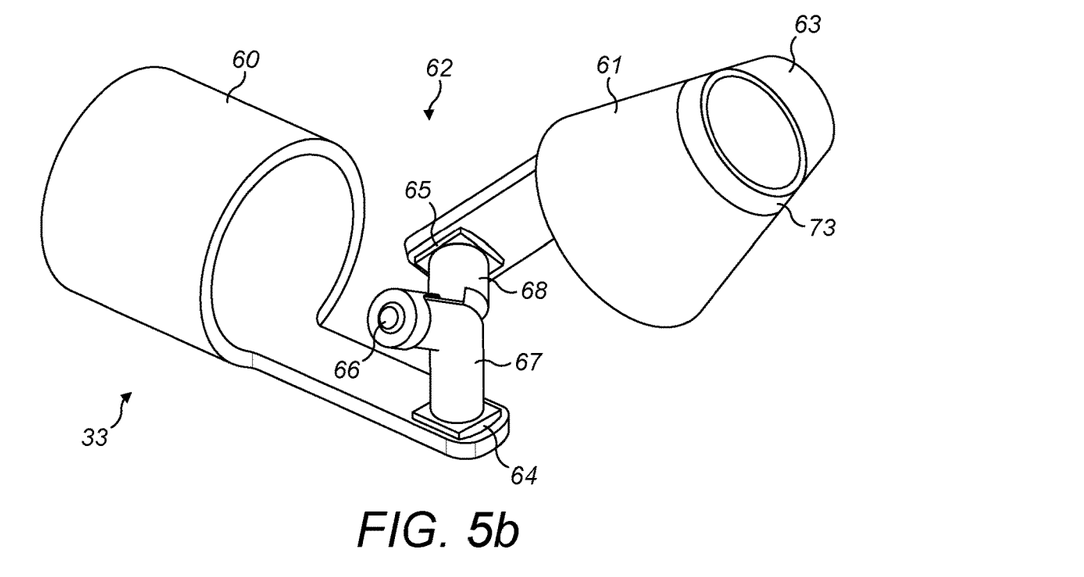
Figure 5C:
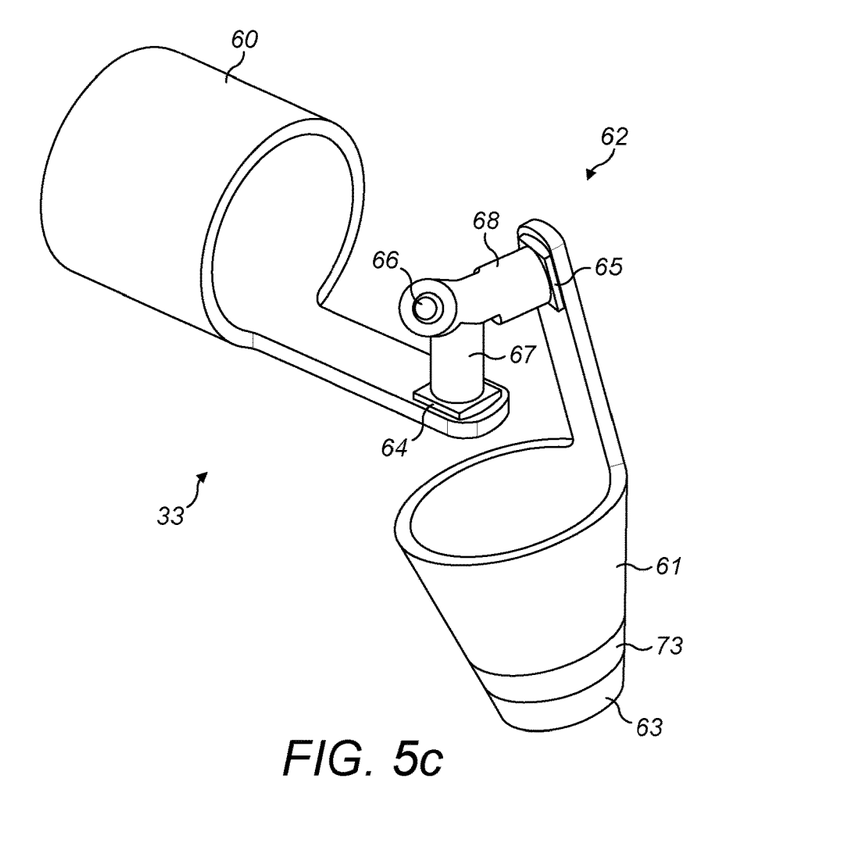

An exemplary wrist portion 33 is shown in more details in FIGS. 5a, 5b and 5c. The wrist portion 33 may be located at the end of the robot arm as shown in FIG. 3 and/or at the end of the instrument as shown in FIG. 4.

FIG. 5a shows the wrist 33 in a straight configuration. The wrist 33 comprises a basal segment 60, a distal segment 61 and an intermediate compound joint 62 between the basal segment and the distal segment. Suitably, when the wrist is located at the end of a robot arm as shown in FIG. 3, the distal segment has an attachment 63 for connecting to a surgical tool, and the basal segment attaches to the remainder of the robot arm. Suitably, when the wrist is located at the end of a surgical instrument as shown in FIG. 4, the distal segment has an attachment 63 for connecting to an end effector, and the basal segment attaches to the instrument shaft 51. The basal and distal segments are rigid.

The compound joint 62 is arranged so as to permit relative rotation of the distal segment 61 and basal segment 60 about three axes: A1, A2 and A3. The compound joint comprises three revolute joints 64, 65 and 66. Revolute joint 64 enables distal segment 61 to rotate about axis A1 relative to the basal segment 60. Revolute joint 65 enables distal segment 61 to rotate about axis A2 relative to the basal segment 60. Revolute joint 66 enables distal segment 61 to rotate about axis A3 relative to the basal segment 60.

Compound joint 62 comprises two intermediate segments 67 and 68. Intermediate segment 67 is coupled to basal segment 60 and intermediate segment 68. Intermediate segment 67 is moveably attached to basal segment 60 and to intermediate segment 68. The relative movement of intermediate segment 67 and basal segment 60 is restricted to a rotation about axis A1. The relative motion of intermediate segment 67 and basal segment 60 is restricted to a revolute motion about axis A1. Suitably, the only way of articulating intermediate segment 67 relative to basal segment 60 is rotation about A1 by means of joint 64.

Intermediate segment 68 is coupled to distal segment 61 and intermediate segment 67. Intermediate segment 68 is moveably attached to distal segment 61 and to intermediate segment 67. The relative movement of intermediate segment 68 and distal segment 61 is restricted to a rotation about axis A2. The relative movement of intermediate segment 68 and distal segment 61 is restricted to a revolute motion about axis A2. Suitably, the only way of articulating intermediate segment 68 relative to distal segment 61 is rotation about A2 by means of joint 65.

Intermediate segment 67 and intermediate segment 68 are moveably attached together. The relative movement of intermediate segment 67 and intermediate segment 68 is restricted to a rotation about axis A3. The relative movement of intermediate segment 67 and intermediate segment 68 is restricted to a revolute motion about axis A3. Suitably, the only way of articulating intermediate segment 68 relative to intermediate segment 67 is rotation about A3 by means of joint 66.

Each intermediate segment 67 and 68 is a rigid link. Intermediate segment 67 comprises two arms 69, 70. The two arms 69 and 70 are held fast together at a relative angle which corresponds to the angle between the axes A1 and A3 when the wrist is in the straight configuration depicted in FIG. 5a. In other words, when the axial directions of the basal segment 60 and the distal segment 61 are aligned, or in the same attitude, the angle between axial directions of arm 69 and arm 70 of intermediate segment 67 is the same as the angle between axes A1 and A3.

Similarly, intermediate segment 68 comprises two arms 71 and 72. The two arms 71 and 72 are held fast together at a relative angle which corresponds to the angle between the axes A2 and A3 when the wrist is in the straight configuration depicted in FIG. 5a. In other words, when the axial directions of the basal segment 60 and the distal segment 61 are aligned, or in the same attitude, the angle between axial directions of arm 71 and arm 72 of intermediate segment 68 is the same as the angle between axes A2 and A3.

Arm 70 of intermediate segment 67 is coupled to arm 72 of intermediate segment 68 such that the motion of arm 72 is constrained to rotation about axis A3 relative to arm 70. In the particular example of FIG. 5, arm 72 embraces arm 70. Arms 70 and 72 are co-axial, and that axis is A3.

Suitably, the only way of articulating the distal segment 61 relative to the basal segment 60 is by motion of the compound joint 62 as described above.

The following describes an exemplary arrangement of the axes A1, A2 and A3. In the arrangement shown in FIG. 5a in which the axial direction of the basal segment 60 is collinear with the axial direction of the distal segment 61, the axes A1, A2 and A3 are transverse to the axial directions of the basal and distal segments. Suitably, the three axes A1, A2 and A3 are coplanar when the wrist 33 is in the configuration of FIG. 5a. That plane is perpendicular to the axial directions of the basal and distal segments. Suitably, the axes A1, A2 and A3 intersect each other at a single point on that plane, or substantially intersect at a single point (e.g. by all intersecting a sphere of radius 50 mm). Suitably, the axes A1, A2 and A3, and hence the arms of the intermediate segments which are aligned along those axes, are equally spaced in that plane. In other words, for three axes A1, A2 and A3, each axis is offset from each of the other axes by 60°, as shown in FIG. 5a.

FIGS. 5b and 5c illustrate the wrist 33 in two different bent configurations, resulting from articulation of compound joint 62 from the straight configuration shown in FIG. 5a. Like parts are indicated by the same references. FIGS. 5b and 5c show examples of posing the wrist relative to the configuration in FIG. 5a by rotation around all three of the joints 64, 65 and 66 about axes A1, A2 and A3 respectively.

The compound joint 62 enables the attachment (which is either (i) the surgical instrument in the case that the wrist 33 is located at the end of the robot arm, or (ii) the end effector in the case that the wrist 33 is located at the end of the surgical instrument) to face any direction in a hemisphere whose base is perpendicular to the axial direction of the basal segment 60.

Each joint of the compound joint 62 may be driven independently of the other joints by one or more motive devices such as electric motors or hydraulic pistons. The motive device(s) may be located locally at the respective joint, or they may be located closer to the base of the robot and coupled to the joints by couplings such as cables or linkages. The motive devices are controllable by a user of the robot.

Figure 6:
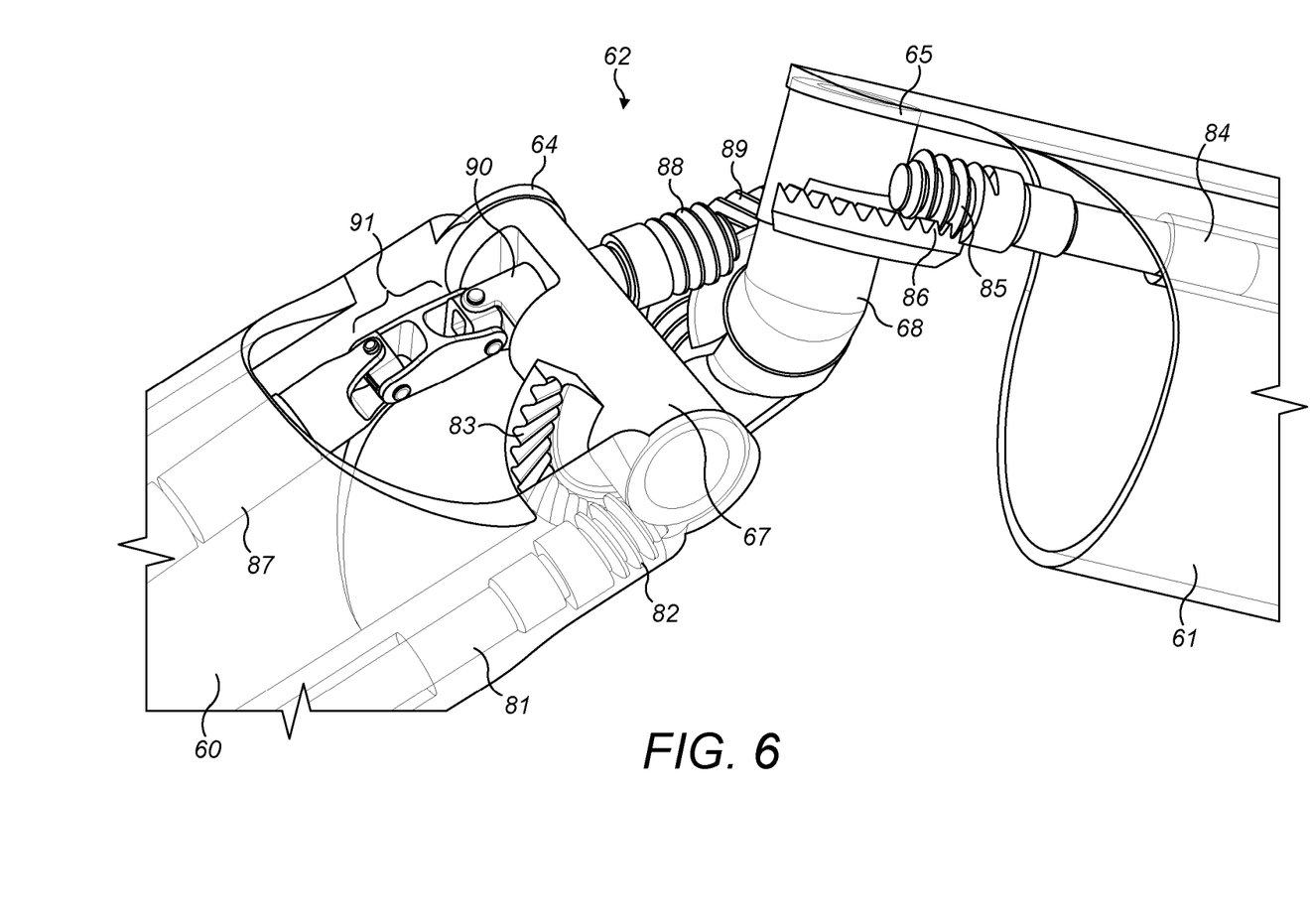
FIG. 6 shows an exemplary configuration in which the robotic wrist component of FIG. 5 can be driven.

FIG. 6 illustrates an exemplary configuration in which joints 64 and 66 are driven from drive shafts extending through the basal segment 60 of the wrist, and joint 65 is driven from a drive shaft extending through the distal segment 61 of the wrist. In the example of FIG. 6, hypoid gears are used to drive the joints. In FIG. 6, like parts to FIG. 5 are indicated by the same references. Joint 64 is driven by drive shaft 81. Drive shaft 81 terminates in worm 82 which engages gear 83. Gear 83 is held fast to intermediate segment 67. Worm 82 holds gear 83 (and hence intermediate segment 67) fast to basal segment 60 unless driven by drive shaft 81. When drive shaft 81 is driven by a motor, it causes worm 82 to rotate, which causes gear 83 to rotate, which causes intermediate segment 67 to rotate about axis A1 relative to the basal segment 60.

Joint 65 is driven by drive shaft 84. Drive shaft 84 terminates in worm 85 which engages with gear 86. Gear 86 is held fast to intermediate segment 68. Worm 85 holds gear 86 (and hence intermediate segment 68) fast to distal segment 61 unless driven by drive shaft 84. When drive shaft 84 is driven by a motor, it causes worm 85 to rotate, which causes gear 86 to rotate, which causes intermediate segment 68 to rotate about axis A2 relative to distal segment 61.

Joint 66 is driven by drive shaft 87. Drive shaft 87 terminates in worm 88 which engages with gear 89. Gear 89 is held fast to intermediate segment 68. Worm 88 holds gear 89 (and hence intermediate segment 68) fast to intermediate segment 67 unless driven by drive shaft 87. When drive shaft 87 is driven by a motor, it causes intermediate segment 68 to rotate about axis A3 relative to intermediate segment 67. In the example shown on FIG. 6, in order to reach gear 89, drive shaft 87 passes through an opening 90 in intermediate segment 67. Drive shaft 87 is articulated using double universal joint 91 so as to cause drive shaft 87 to cooperate with motion of the joints 64 and 65 of the compound joint 62. The double universal joint 91 (also known as a DV joint) counteracts motion caused to drive shaft 87 when joint 64 and/or joint 66 is articulated so as to enable worm 88 to remain engaged with gear 89. A helical universal joint may be used instead of a double universal joint. In an alternative arrangement, drive shaft 87 may reach gear 89 by articulating around intermediate segment 67. Alternatively, an offset hypoid gear may be used for driving joint 66 so as to avoid passing drive shaft 87 through intermediate segment 67. In an alternative example to that shown in FIG. 6, gear 89 may be held fast to intermediate segment 67 and not to intermediate segment 68, and hence, when driven, cause intermediate segment 67 to rotate about axis A3 relative to intermediate segment 68.

The wrist 33 of FIGS. 5 and 6 has a kinematic redundancy. Compound joint 62 could consist of only two joints which are transverse both to each other and the basal and distal segments. However, it has been found that when the compound joint consists of only two joints which permit motion transverse to each other and the axial direction of the basal segment, the bend angle of the distal segment relative to the basal segment is limited to about 60°. However, by using an additional joint in compound joint 62 such that basal and distal segments are rotatable about the three axes A1, A2 and A3, it has been found that a wider range of motion results, with a bend angle of up to 120°. In practice, when motion about one axis reaches the end of its travel, motion about another axis can continue the motion. Additionally, the kinematic singularity described above is eliminated. Additionally, there is often more than one way in which the joints can be articulated to get from a first orientation of wrist 33 to a second orientation of wrist 33. Conveniently, the path taken is the one that minimises the total joint motion. Thus, the robotic component that the wrist is located in does not need as much space around it to be able to articulate to its possible positions. In the case of a robot arm as shown in FIG. 3, this can make it easier to position the bases of multiple robots around an operating site because surgical staff have more freedom over where to locate the robot bases. It can also help to avoid the need to redesign existing operating room workflows to accommodate a robot. It can also improve the accessibility of multiple such arms to an operation site, especially a site for a procedure such as an ENT (ear, nose and throat) procedure where typically multiple instruments must access the operation site through a small opening. In the case of a surgical instrument, this may allow space for a further surgical instrument to be used in the operation, for example in an ENT procedure where space for the instruments inside the body is very limited.

The wrist 33 is capable of a large bend angle, but is still slim and lightweight. The compact arrangement of joints in compound joint 62 are much lighter weight than alternative joint configurations which achieve a comparable bend angle. For example, a double universal joint can be used to achieve a comparable bend angle, but is significantly more complex in structure and heavier. The more lightweight the compound joint 62, the less stiff the shafts of the robot arm and instrument need to be to support the compound joint, and hence the lighter weight the whole robot can be. This makes the robot easier to move around the operating theatre and set up for use. Further joints could be used in the compound joint to further increase the redundancy and hence the range of motion of the compound joint. However, further joints add weight and complexity. Additional drive shafts may be required to drive the additional joints.

Although FIG. 6 shows the constituent joints of the compound joint 62 being driven using hypoid gears, other gearing may be used, for example spiroid gears, bevel gears, conventional robotic drives etc. Suitably, each joint of the compound joint 62 is driven using the same gearing.

Suitably, the wrist 33 of FIG. 5 comprises a further revolute joint 73 attached to the distal end of the distal segment. Joint 73 permits the attachment to rotate about axis A4 relative to the remainder of the wrist 33. Axis A4 is the axial direction of distal segment 61. In the configuration of FIG. 5a, the axis A4 conveniently intersects or substantially intersects (e.g. within 50 mm) axes A1, A2 and A3 at a single point. Suitably, the only means of articulating the attachment relative to the basal segment are the compound joint 62 and the joint 73.

For the case that the wrist 33 is at the terminal end of the robot arm, as shown in FIG. 3, the instrument base 52 is designed cooperatively with the end of the robot arm so that the instrument base can be releasably attached to the robot arm with the shaft 51 extending away from the instrument base. Conveniently the shaft 51 extends away from the instrument base in a direction that is parallel or substantially parallel and/or coaxial or substantially coaxial with axis A4 of the distal segment 61. This means that the end effector 54 has substantial range of movement by virtue of the joints of the wrist 33 of the robot arm, and that the joints of the wrist 33 can be used conveniently to position the end effector. This arrangement can permit the end effector to be readily rotated to a desired orientation through motion of the wrist without excessively disrupting a wound channel in the patient. The fact that the elongation of the instrument shaft extends away from the wrist as described above means that the wrist has a degree of articulation that is similar to the wrist of a human surgeon. One result of that is that many surgical techniques practised by humans can readily be translated to motions of this robot arm. This can help reduce the need to devise robot-specific versions of known surgical procedures.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A surgical robotic component comprising an articulated terminal portion, the terminal portion comprising:
    a distal segment having an attachment configured to attach a surgical tool;
    a basal segment configured to attach the terminal portion to the remainder of the surgical robotic component; and
    an intermediate compound joint connecting the distal segment to the basal segment, wherein the intermediate compound joint comprises exactly two rigid intermediate segments including a first rigid intermediate segment and a second rigid intermediate segment, and wherein (i) the first rigid intermediate segment is coupled to the basal segment and to the second rigid intermediate segment and (ii) the second rigid intermediate segment is coupled to the distal segment and to the first rigid intermediate segment, and further wherein the intermediate compound joint is configured to permit relative rotation of the distal segment and the basal segment about first, second and third axes;
    the terminal portion being arranged such that, in at least one configuration of the intermediate compound joint: (i) the axial direction of the basal segment is collinear to the axial direction of the distal segment, and (ii) the first, second and third axes are transverse to the axial directions of the basal and distal segments, wherein
    in the at least one configuration of the intermediate compound joint, the first, second and third axes are co-planar with each other.

2. A surgical robotic component as claimed in claim 1, wherein in the at least one configuration of the intermediate compound joint, the first, second and third axes are perpendicular to the axial directions of the basal and distal segments.

3. A surgical robotic component as claimed in claim 1, wherein the first, second and third axes intersect each other.

4. A surgical robotic component as claimed in claim 1, wherein the first, second and third axes are co-planar with each other and offset from each other in that plane by 60°.

5. A surgical robotic component as claimed in claim 1, wherein the intermediate compound joint comprises:
    a first revolute joint which enables the distal segment to rotate about the first axis relative to the basal segment;
    a second revolute joint which enables the distal segment to rotate about the second axis relative to the basal segment; and
    a third revolute joint which enables the distal segment to rotate about the third axis relative to the basal segment.

6. A surgical robotic component as claimed in claim 5, wherein the first, second and third revolute joints are arranged to be independently driven.

7. A surgical robotic component as claimed in claim 6, comprising: a first drive shaft located in the basal segment configured to drive the first revolute joint, a second drive shaft located in the distal segment configured to drive the second revolute joint, and a third drive shaft located in the basal segment configured to drive the third revolute joint.

8. A surgical robotic component as claimed in claim 5, wherein the terminal portion comprises an additional revolute joint between the distal segment and the attachment, which permits rotation of the attachment about the axial direction of the distal segment.

9. A surgical robotic component as claimed in claim 8, wherein the attachment can only be articulated relative to the basal segment by the intermediate compound joint and the additional revolute joint.

10. A surgical robotic component as claimed in claim 1, wherein the first rigid intermediate segment comprises a basal arm portion coupled to the basal segment such that motion of the basal arm portion is restrained to rotation about the first axis relative to the basal segment.

11. A surgical robotic component as claimed in claim 1, wherein the second rigid intermediate segment comprises a distal arm portion coupled to the distal segment such that motion of the distal arm portion is restrained to rotation about the second axis relative to the distal segment.

12. A surgical robotic component as claimed in claim 1, wherein the first rigid intermediate segment comprises a first connecting arm portion and the second rigid intermediate segment comprises a second connecting arm portion, the first connecting arm portion coupled to the second connecting arm portion such that motion of the first connecting arm portion is restrained to rotation about the third axis relative to the second connecting arm portion.

13. A surgical robotic component as claimed in claim 1, wherein the surgical robotic component is a surgical robot arm.

14. A surgical robotic component as claimed in claim 13, wherein the surgical tool is a surgical instrument which terminates in a surgical end effector.

15. A surgical robotic component as claimed in claim 1, wherein the surgical robotic component is a surgical instrument configured to be driven by a surgical robot arm.

16. A surgical robotic component as claimed in claim 15, wherein the surgical tool is a surgical end effector.

* * * * *